United States Patent [19]

Burl et al.

[11] Patent Number: 4,520,828

[45] Date of Patent: Jun. 4, 1985

[54] NUCLEAR MAGNETIC RESONANCE METHOD AND APPARATUS

[75] Inventors: Michael Burl, Hampton Hill; Ian R. Young, Sunbury-on-Thames, both of England

[73] Assignee: Picker International, Ltd., Wembley, England

[21] Appl. No.: 518,215

[22] Filed: Jul. 28, 1983

[30] Foreign Application Priority Data

Aug. 11, 1982 [GB] United Kingdom ............... 8223115

[51] Int. Cl.$^3$ ............................................. A61B 5/05
[52] U.S. Cl. ................................. 128/653; 324/306; 324/309
[58] Field of Search ..................... 128/653, 601, 1.5; 324/306, 309

[56] References Cited

U.S. PATENT DOCUMENTS 4,354,499 10/1982 Damadian ........................ 128/653

OTHER PUBLICATIONS

Singer, Jr., NMR Flow Imaging, Proceedings of an International Symposium on NMR Imaging, Bowman Gray School of Medicine of Wake Forest Univ., Winston-Salem, N.C., Oct. 1-3, 1981.
Battocletti, J. H., "Flat Crossed-Coil Detector for Blood Flow Measurement Using Nuclear Magnetic Resonance", Med. & Bio. Engr. & Comp., Mar. 1979, No. 2, pp. 183-191.

Primary Examiner—Kyle L. Howell
Assistant Examiner—Francis J. Jaworski
Attorney, Agent, or Firm—Watts, Hoffmann, Fisher & Heinke Co.

[57] ABSTRACT

A method and apparatus for determining the rate of flow of a liquid in a selected region of a body by nuclear magnetic resonance techniques. The method includes a sequence of applying a first magnetic pulse ($B_1(90°)$) effective to excite nuclear magnetic resonance of a chosen nucleus within the liquid preferentially in a slice of the body which includes the selected region. A period of time ($t_D$) is waited and then a second magnetic pulse ($B_1(90°)$) is applied which is effective to excite nuclear magnetic resonance of the nuclei preferentially in the slice, and the free induction decay signal is measured. The whole sequence is repeated for different values of the period of time ($t_D$). The values of the period of time ($t_D$) and the corresponding measured signals are then related to the rate of flow of the liquid through the slice.

7 Claims, 4 Drawing Figures

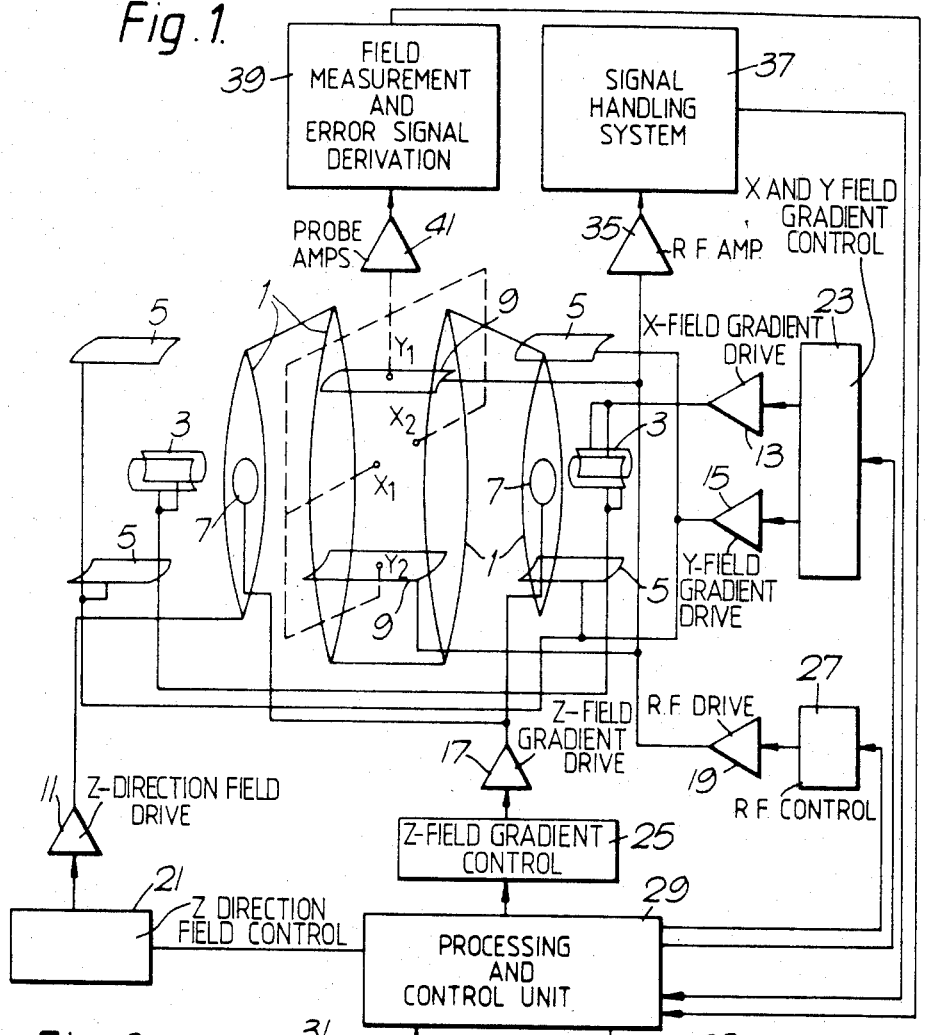
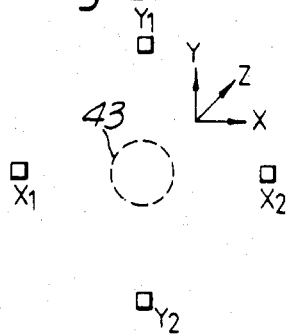

NUCLEAR MAGNETIC RESONANCE METHOD AND APPARATUS

This invention relates to methods and apparatus for determining the rate of flow of a liquid in a selected region of a body by nuclear magnetic resonance (NMR) techniques.

NMR techniques have been used for the chemical analysis of material for many years. More recently NMR techniques have been used to obtain images representing the distribution over a selected cross-sectional slice or volume of a body of a chosen quantity, e.g. the density of chosen nuclei, for example hydrogen protons, or of NMR spin relaxation time constants. Such distributions are similar to, although of different significance from, the distribution of X-ray attenuation provided by computerized tomography systems. In some applications it would be useful to obtain additional information relating to the flow rates of a liquid within a selected region of the body, e.g. blood flow in selected veins and arteries of a human body, using NMR techniques.

It is an object of the invention to provide a method of determining the rate of flow of a liquid in a selected region of a body by NMR techniques.

According to the present invention a method of determining the rate of flow of a liquid including a chosen nucleus in a region of a body comprises: sequentially applying a first magnetic pulse effective to excite nuclear magnetic resonance of said nuclei preferentially in a slice of said body which includes said region, waiting a period of time and then applying a second magnetic pulse effective to excite nuclear magnetic resonance of said nuclei preferentially in said slice and measuring the free induction decay signal; repeating said sequence for different values of said period of time; and relating the values of said period of time and the corresponding measured signals to the rate of flow of said liquid through said slice.

The invention also provides an apparatus arranged to carry out a method according to the invention, including means arranged to sequentially apply a first magnetic pulse effective to excite nuclear magnetic resonance of said nuclei preferentially in a slice of said body which includes said region, wait a period of time and then apply a second magnetic pulse effective to excite nuclear magnetic resonance of said nuclei preferentially in said slice and measure the free induction decay signal and repeat said sequence for different values of said period of time.

One method and apparatus in accordance with the invention will now be described, by way of example only with reference to the accompanying drawings in which:

FIGS. 1 and 2 illustrate the apparatus diagramatically;

Figure 3:
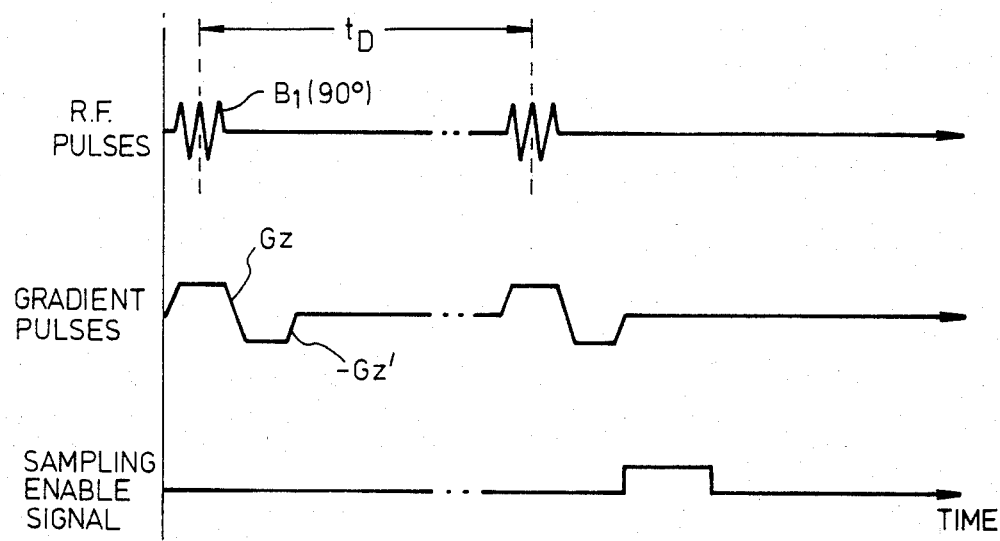
FIG. 3 illustrates the magnetic field sequence employed in the method.

The method is performed using an apparatus such as that described in U.K. Pat. Nos. 1,578,910 or 2,056,078, to which reference should be made for a fuller description, appropriately configurred to apply a sequence of magnetic field gradient and R.F. pulses and analyse the resulting signals as hereafter described.

The essential features of such an apparatus in so far as is required for an understanding of the present invention are as follows:

The apparatus includes a first coil system whereby a magnetic field can be applied to a body to be examined in a given direction, normally designated the Z-direction, with a gradient in any one or more of the three orthogonal directions i.e. X, Y and Z directions.

Referring to FIG. 1, the first coil system comprises coils 1 capable of providing a steady uniform magnetic field in the Z direction; coils 3 capable of providing a magnetic field gradient in the X direction, coils 5 capable of providing a magnetic field gradient in the Y direction; and coils 7 capable of providing a magnetic field gradient in the Z direction.

In addition, the apparatus includes a second coil system 9 whereby RF magnetic fields can be applied to the body under examination in a plane normal to the direction of the steady uniform magnetic field produced by the first coil system, and whereby RF magnetic fields resulting from nuclei in the body under examination which have been excited to nuclear magnetic resonance with a spin vector component other than in the Z direction can be detected.

In the drawing a single pair of coils 9 is shown for both applying and detecting RF fields, but in certain circumstances it may be preferable to provide separate coils for detecting the RF fields.

The various coils 1, 3, 5, 7 and 9 are driven by drive amplifiers 11, 12, 13, 15, 17 and 19 respectively, controlled by control circuits 21, 23, 25 and 27 respectively. These circuits may take various forms which are well known to those with experience of NMR equipment and other apparatus using coil induced magnetic fields.

The circuits 21, 23, 25 and 27 are controlled by a central processing and control unit 29 with which are associated inputs and other peripherals 31, for the provision of commands and instructions to the apparatus, and a display 33.

The NMR signals detected by the coils 9 are applied via an amplifier 35 to a signal handling system 37. The signal handling system is arranged to make any appropriate calibration and correction of the signals, but essentially transmits the signals to the processing and control unit 29 wherein the signals are processed for application to the display to produce an image representing the distribution of an NMR quantity in the body being examined.

It will be appreciated that whilst shown separately to clarify the present description, the signal handling system 37 may conveniently form part of the unit 29.

The apparatus also includes field measurement and error signal circuits 39 which receive signals via amplifiers 41 from field probes $X_1$, $X_2$, $Y_1$ and $Y_2$ which are disposed at suitable positions in relation to a slice 43 of the body being examined, as illustrated in FIG. 2, to monitor the applied magnetic fields.

Referring now also to FIG. 3, in operation of the apparatus a steady uniform magnetic field Bo is applied to the body under examination in the Z direction. This field serves to define the equilibrium axis of magnetic alignment of the nuclei in the body i.e. along the Z direction, and remains constant throughout the examination procedure. A magnetic field gradient Gz along the Z direction is then applied to the body, together with an RF magnetic field pulse denoted $B_1(90°)$, for reasons explained hereafter. The frequency of the RF field is chosen to be the Larmor frequency for hydrogen protons in a slice 43 of the body, normal to the Z direction, the slice being defined by a particular magnetic field along the Z direction, such that hydrogen protons within the slice are preferentially excited, the slice consisting of an area of substantially solid material through which a series of blood vessels extend. The integral of the RF pulse is such that the pulse is just sufficient to tip the spins of the excited protons into the X-Y plane, and is thus referred to as a 90° pulse, the spins then precessing in the X-Y plane round the Z axis.

The field gradient Gz is then removed, and replaced by a field gradient in the opposite sense—Gz′. This causes the rephasing of the spins which have been selectively excited by the combination of the RF pulse $B_1(90°)$, Bo and the field gradient Gz the dephasing having been caused by the gradient through the slice. The magnitude of —Gz′ is adjusted so that the spins are rephased at the time at which this field gradient is switched off as described, for example, in the above mentioned U.K. Pat. No. 1,578,910.

After a time $t_D$ has elapsed since the pulse $B_1(90°)$, a second $B_1(90°)$ pulse is applied together with the field gradient Gz. this again being followed by the field gradient—Gz′. The signal induced in the second coil system 9 by the excited protons in the slice, i.e. the free induction decay (F.I.D.) signal is then recorded. This double excitation sequence is then repeated a number of times with the time $t_D$ between the successive excitation pulses $B_1(90°)$ being varied through a range of values.

Figure 4:
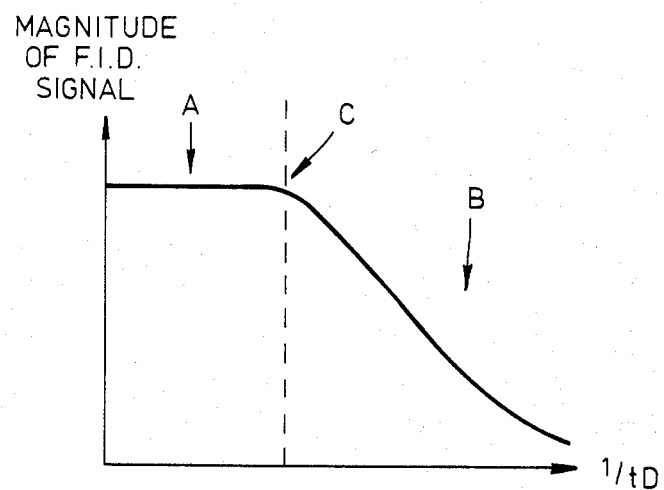
FIG. 4 is a graphical illustration of the relationship between the measured free induction decay signal and the repetition rate of the magnetic field sequence.

Referring now also to FIG. 4, a graph is plotted of the magnitude of the F.I.D. signals measured, i.e. an indication of the density of the excited nuclei within the slice, against the excitation pulse repetition frequency, $1/t_D$. As $t_D$ is always chosen to be much shorter than the spin-lattice relaxation time $T_1$ for hydrogen protons within the slice, the excited nuclei do not have time to relax back to their equilibrium spin orientation along the Z direction. Thus the second $B_1(90°)$ pulse will remove spins remaining in the X-Y plane into the—Z direction, these spins then not contributing to the measured F.I.D. signal. In the case of blood within the vessels in the slice however, blood which was initially in the slice during the first $B_1(90°)$ pulse, and has subsequently flowed out of the slice during the period $t_D$, is replaced by fresh blood having unexcited hydrogen protons prior to the second $B_1(90°)$ pulse. Thus after excitation by the second $B_1(90°)$ pulse, these 'fresh blood' spins contribute to the F.I.D. measured. For long values of $t_D$, i.e. a low excitation pulse repetition rate $1/t_D$, the blood has time to be completely replaced within the slice, and thus the plateau region A of the graph shown in FIG. 4 is achieved. As the excitation pulse repetition rate $1/t_D$, increases, however, the blood does not have time to be completely replaced, and thus after a certain value of $1/t_D$ the FID signal begins to decrease with a further increase in $1/t_D$ as shown in region B of the graph. The shoulder C indicated on the graph at the crossover point between the regions A and B thus gives an indication of the minimum time period during which blood is completely replaced within the slice, and from this the flow rate of the blood through the vessels in the slice can be calculated.

It is found that this method is suitable for measuring flow rates for blood which is replaced within a slice in the time range 0.1 to 1.0 seconds.

In the double excitation sequence described herebefore, the F.I.D. signal is not recorded after the first excitation pulse $B_1(90°)$ in each sequence. It will be appreciated however that in a continuous repetition of this sequence it may be more convenient to record the F.I.D. signal after the second excitation pulse and then after each subsequent excitation pulse, with $t_D$ being the interval between successive excitation pulses. A correction to the measured F.I.D.s will then have to be made to compensate for spins which are not aligned along the equilibrium direction Z during the first excitation pulse in each pair of pulses.

It will also be appreciated that within each repetition time $t_D$ known NMR imaging techniques using magnetic field gradients in the X and Y directions may be employed in order to obtain information relating to the spatial distribution over the chosen slice of quantities relating to nuclear magnetic resonance, e.g. the density of a nucleus, or NMR spin relaxation time constants.

It will be appreciated that whilst the method described herebefore relates to obtaining the flow rate of a liquid which includes hydrogen protons, the method is equally applicable to obtaining the flow rate of a liquid including any other nucleus having a spin, e.g. $^{31}P$, by appropriate choice of the R.F. pulse frequency.

I claim:

1. A method of determining the rate of flow of a liquid in a region of a body comprising: sequentially applying a first magnetic pulse effective to cause nuclei preferentially in a slice of said body which includes said region to emit a first free induction decay signal, waiting a period of time less than the spin-lattice relaxation time for said chosen nuclei in said slice and then applying a second magnetic pulse effective to cause nuclei preferentially in said slice to emit a second free induction decay signal and measuring said second free induction decay signal; repeating said sequence for different values of said period of time; and relating the values of said period of time and the corresponding measured signals to the rate of flow of said liquid through said slice.

2. A method according to claim 1 in which said first and second magnetic pulses are each sufficient to rotate the spins of said nuclei through an angle of substantially 90°.

3. A method according to claim 1 in which said second free induction decay signal is measured after said second magnetic pulse, and then each subsequent free induction decay signal is measured.

4. A method according to claim 1 in which nuclear magnetic resonance imaging techniques are employed during said period of time in order to obtain information relating to the spatial distribution over said slice of quantities relating to nuclear magnetic resonance.

5. A method according to claim 1 in which said relating comprises determining the minimum value of said time period which is sufficient for said liquid to be completely replaced in said slice by the time of the next excitation.

6. A method according to claim 5 in which said relating comprises determining the reciprocal of the value of said period of time at which said measured signal begins to decrease for increasing values of the reciprocal of the values of said period of time.

7. A system for determining the rate of flow of a liquid in a region of a body, said system comprising
   (a) first apparatus and circuitry for applying a first magnetic pulse effective to cause nuclei, preferentially in a slice of said body which includes said region, to emit a first free induction decay signal, (b) a processing and control unit comprising control circuitry for actuating said first apparatus and circuitry for applying a second magnetic pulse at a time increment following said first magnetic pulse of less than the spin-lattice relaxation time for nuclei in said slice for causing nuclei preferentially in said slice to emit a second free induction decay signal;

(c) sensing apparatus and circuitry for measuring said second free induction decay signal, and (d) said sensing and said control apparatus and circuitry comprising circuitry for repeating the sequence of application of said first and second magnetic pulses and for measuring said second free induction decay signal for different values of said time increment.

* * * * *